Figure 1:
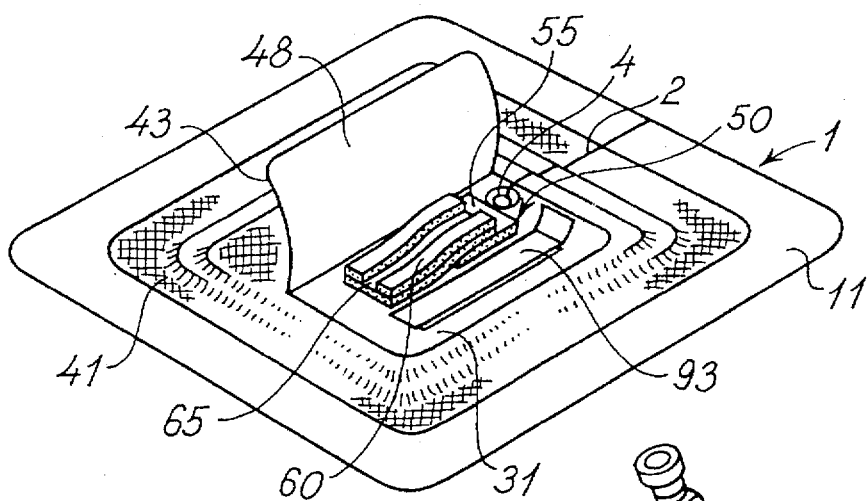

United States Patent [19]
Kornerup

[11] Patent Number: 5,685,859
[45] Date of Patent: Nov. 11, 1997

[54] DEVICE FOR FIXATING A DRAINAGE TUBE AND A DRAINAGE TUBE ASSEMBLY

[75] Inventor: Niels Kornerup, Roedovre, Denmark

[73] Assignee: Nikomed Aps, Roedovre, Denmark

[21] Appl. No.: 454,518

[22] Filed: May 30, 1995

[30] Foreign Application Priority Data

Jun. 2, 1994 [DK] Denmark ..................... 94 00241
Jan. 13, 1995 [DK] Denmark ........................... 39/95

[51] Int. Cl.$^6$ ............................................. A61M 11/00
[52] U.S. Cl. .................................. 604/180; 604/179
[58] Field of Search ............................. 604/174, 179, 604/180; 128/DIG. 26

[56] References Cited

U.S. PATENT DOCUMENTS 4,645,492 2/1987 Weeks ............................ 604/174

FOREIGN PATENT DOCUMENTS

WO91/07204 5/1991 WIPO.
WO93/17738 9/1993 WIPO.
WO93/25264 12/1993 WIPO.

Primary Examiner—Sam Rimell
Attorney, Agent, or Firm—Thomas R. Vigil

[57] ABSTRACT

A device for fixating a drainage tube relative to a skin surface part of a patient or person comprises a plaster component including a support foil having an aperture for receiving said drainage tube, and opposite first and second side surfaces, said first side surface being provided with an adhesive layer for fixating said plaster component relative to said skin surface part of said patient or person, a support component arranged adjacent said aperture at said second side surface of said plaster component and protruding therefrom, said support component having an outer surface for supporting a length of said drainage tube extending from said aperture at said second side surface of said plaster component so as to turn said length of said drainage tube in supported relationship with said support component from an orientation substantially perpendicular to said skin surface part of said patient or person to an orientation substantially parallel with said skin surface part of said patient or person, and said support component and said plaster component being joined together.

12 Claims, 8 Drawing Sheets

DEVICE FOR FIXATING A DRAINAGE TUBE AND A DRAINAGE TUBE ASSEMBLY

The present invention generally relates to the technique of applying and fixating a tube, such as a drainage tube, relative to a skin surface part of a patient or person, and more precisely a device for fixating such a tube relative to a skin surface part of a patient or person.

It is a well-known technique to enter a drainage tube through the skin of a patient or person in order to drain liquid from a cavity within the patient or person, e.g. after a surgical operation. In certain applications, the drainage tube is also used for creating a vacuum within the cavity which is drained by means of the drainage tube. An example of such an application is the treatment of a collapsed lung, in which application the cavity of the thorax of the patient in question is evacuated through a pleural drainage tube in order to cause an adhesion of the pulmonary pleura of the patient to the costal pleura of the patient. In all applications of drainage tubes, there exists a risk that the drainage tube is blocked as the drainage tube is bent, or kinks of the drainage tube are produced.

Provided the drainage tube is to be vented for creating a vacuum within the cavity which is vented through the drainage tube, a further problem exists in creating a reliable and lasting sealing of the entrance of the drainage tube through the skin of the patient, and further an overall desire of rendering it possible to create a sealing and a fixation of the drainage tube in a swift and reliable manner. Hitherto, the drainage tube, such as a pleural drainage tube which is used for venting the cavity of the thorax of the patient, the lung of whom has collapsed, has been fixated and sealed in a manual operation in which the medical doctor who applies the pleural drainage tube arranges one or more vaseline-impregnated wads round the pleural drainage tube at the entrance of the pleural drainage tube through the skin of the patient and compresses the vaseline-impregnated wads in order to create a sealing at the entrance. Thereupon, the vaseline-impregnated wads and the pleural drainage tube as well are fixated by means of plaster.

The technique of applying and fixating a drainage tube, in particular a venting drainage tube, such as a pleural drainage tube, is a complex and time-consuming operation which requires skill and which further often turns out to be inadequate and inappropriate as the sealing of the entrance of the pleural drainage tube through the skin of the patient in question leaks, causing great harm to the patient.

Various devices for fixating a drainage tube have recently been developed as disclosed in eg. U.S. Pat. No. 4,419,094 or WO 93/25264. When using these known devices, a proximal part of the drainage tube extending from the body of the patient through a through-going passage in the device, is bent to form a loop whereby a distal part of the tube is fixated to the skin surface of the patient by means of eg. a separate piece of plaster. This procedure, however, gives rise to a potential risk of the tube becoming blocked if the tube is inadvertently doubled or bent upon itself.

An object of the present invention is to provide a device for fixating a drainage tube, which device to any substantial extent eliminates the risk that the drainage tube is blocked at the entrance of the skin of the patient in question by to any substantial extent eliminating the risk of creation of kinks of the drainage tube.

An advantage of the device according to the present invention lies in that a single unitary structure is provided which renders it possible, in a single and easily performable operation, to create a fixation of the drainage tube and also create a sealing of the entrance of the drainage tube through the skin of the patient while at the same time ensuring that the tube is not bent upon itself in the region of its entry to the patient.

A feature of the device according to the present invention lies in that the device according to the present invention constitutes a disposable unitary strucure which has been presterilized and simply is applied as a plaster structure to the skin of the patient.

The above object, the adore advantage, and the above feature together with numerous other objects, advantages, and features which will be evident from the below detailed description of preferred embodiments of the device according to the present invention are obtained by means of a device for fixating a drainage tube relative to a skin surface part of a patient or person, comprising in accordance with the present invention:

a device for fixating a drainage tube relative to a skin surface part of a patient or person, comprising:

a plaster component including a support foil having an aperture for receiving said drainage tube, and opposite first and second side surfaces, said first side surface being provided with an adhesive layer for fixating said plaster component relative to said skin surface part of said patient or person, a support component arranged adjacent said aperture at said second side surface of said plaster component and protruding therefrom, said support component having an outer surface for supporting a length of said drainage tube extending from said aperture at said second side surface of said plaster component so as to turn said length of said drainage tube in supported relationship with said support component from an orientation substantially perpendicular to said skin surface part of said patient or person to an orientation substantially parallel with said skin surface part of said patient or person, and said support component and said plaster component being joined together.

The support component of the device according to the present invention fulfils the main purposes of turning the length of the drainage tube which length extends outwardly from the aperture of the plaster component and outwardly from the skin surface part of the person or patient to which skin surface part the device is fixated by means of the plaster component from an orientation substantially perpendicular to the skin surface part of the patient or person to an orientation substantially parallel with the skin surface part of the patient or person and also of preventing the tube from being blocked by the turning from the above perpendicular orientation to the above parallel orientation or through the generation of kinks or bends on the drainage tube. A basic realization of the present invention relates to the fact that a drainage tube extending substantially perpendicularly out from the skin surface part of the patient or person is to a high degree exposed to mechanical impact which may on the one hand generate kinks on the drainage tube and on the other hand cause the drainage tube to be removed from its intentional position relative to the skin surface part and the interior of the patient or person to whom the drainage tube is fixated. Furthermore, it has in accordance with the teachings of the present invention been realized that the human body to a high degree attempts to expell foreign bodies such as drainage tubes which are introduced into the interior of the human body and the autonomous expelling of a drainage tube form the human body is to a high degree eliminated provided the drainage tube is fixated in an orientation parallel with the skin surface part of the patient or person as compared to an orientation perpendicular to the skin surface part of the patient or person through which skin surface part the drainage tube extends. Preferably, in accordance with the basic realisation of the present invention, the outer surface of the support component is rounded for supporting the length of the tube in a curved configuration.

According to a first embodiment, a connecting component carries the support component, the plaster component and the support component being joined together by means of the connecting component being fixated to the first side surface of the plaster component. In order to provide a reliable fixation of the device according to the present invention, and consequently of the drainage tube relative to the skin surface part of the patient in question, the surface part of the connecting component may be provided with an adhesive layer for adhering to the skin surface part of the patient or person. Preferably, the adhesive layer of the connecting component is a biologically acceptable and/or compatible glue layer, such as a medical grade acrylic adhesive layer or a hydro-colloid layer which is glued to the surface part of the connecting component by means of e.g. an adhesive layer, a glue or the like. The connecting component may have a rectangular or a curved outline or any alternative appropriate configuration fulfilling the basic object of the present invention.

The plaster component of the device according to the present invention may be of any appropriate configuration, serving the purpose of providing a reliable and lasting fixation of the flange part of the support component relative to the skin surface part of the patient.

The support component may, according to a second embodiment particularly adapted for pleural drainage tubes, be formed from a sponge-like material of a biologically non-aggressive and wound-care or wound-treatment compatible material, and having an aperture through which the drainage tube is passed. According to this second embodiment of the invention, the support component may be attached to the second or upper side surface of the plaster, the plaster being formed with a relatively large through-going aperture and the aperture of the support component being in registration with the aperture of the plaster component. The device may further comprise sealing means for sealing round the aperture of the plaster component relative to the outer periphery of the drainage tube.

The device according to the present invention may comprise securing means for fixating the drainage tube in a plane substantially parallel to the plaster component. The securing means may be formed as an integral part of the support component or may comprise an adhesive strip provided with transparent apertures for checking the correct positioning of the drainage tube relative to the patient, i.e. for checking that the tube has not shifted, and for checking the condition of the opening in the body of the patient. It is to be realized that in case the drainage tube does not remain correctly positioned relative to the patient, great harm may in some instances be incurred to the patient as e.g. the vacuum which is created within the cavity in the treatment of e.g. a collapsed lung may result in extremely dangerous and harmful subcutaneous swelling of large areas of the chest and face of the patient, provided some air unintentionally is subcutaneously vented.

Figure 2:
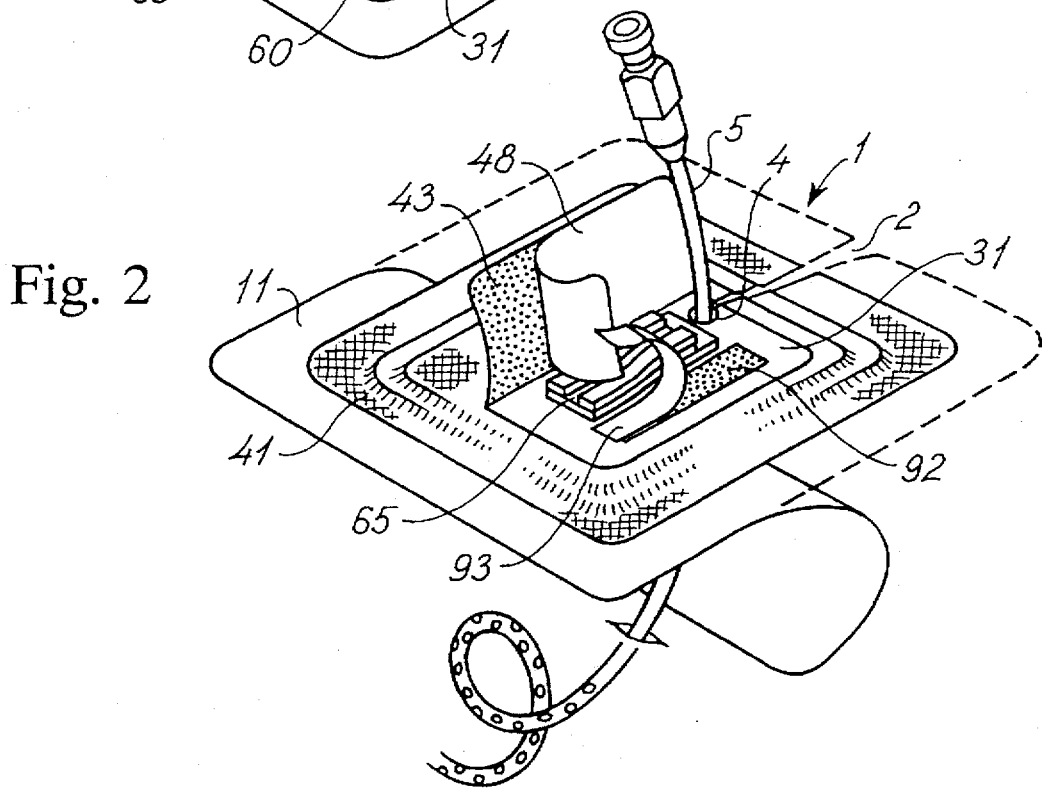
Figure 3:
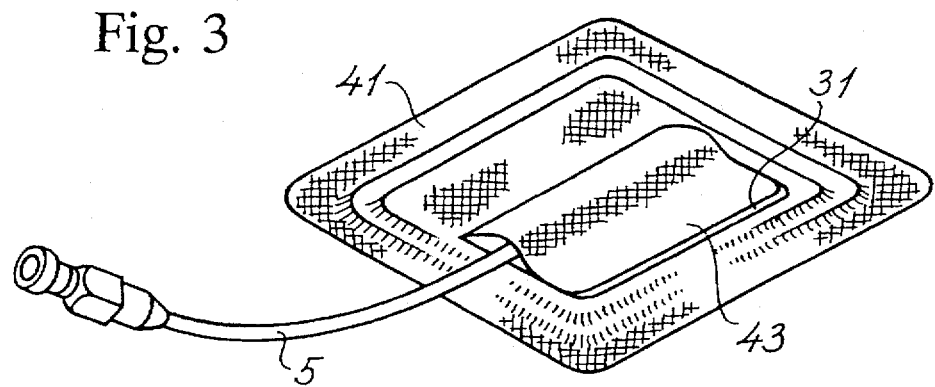
Figure 4:
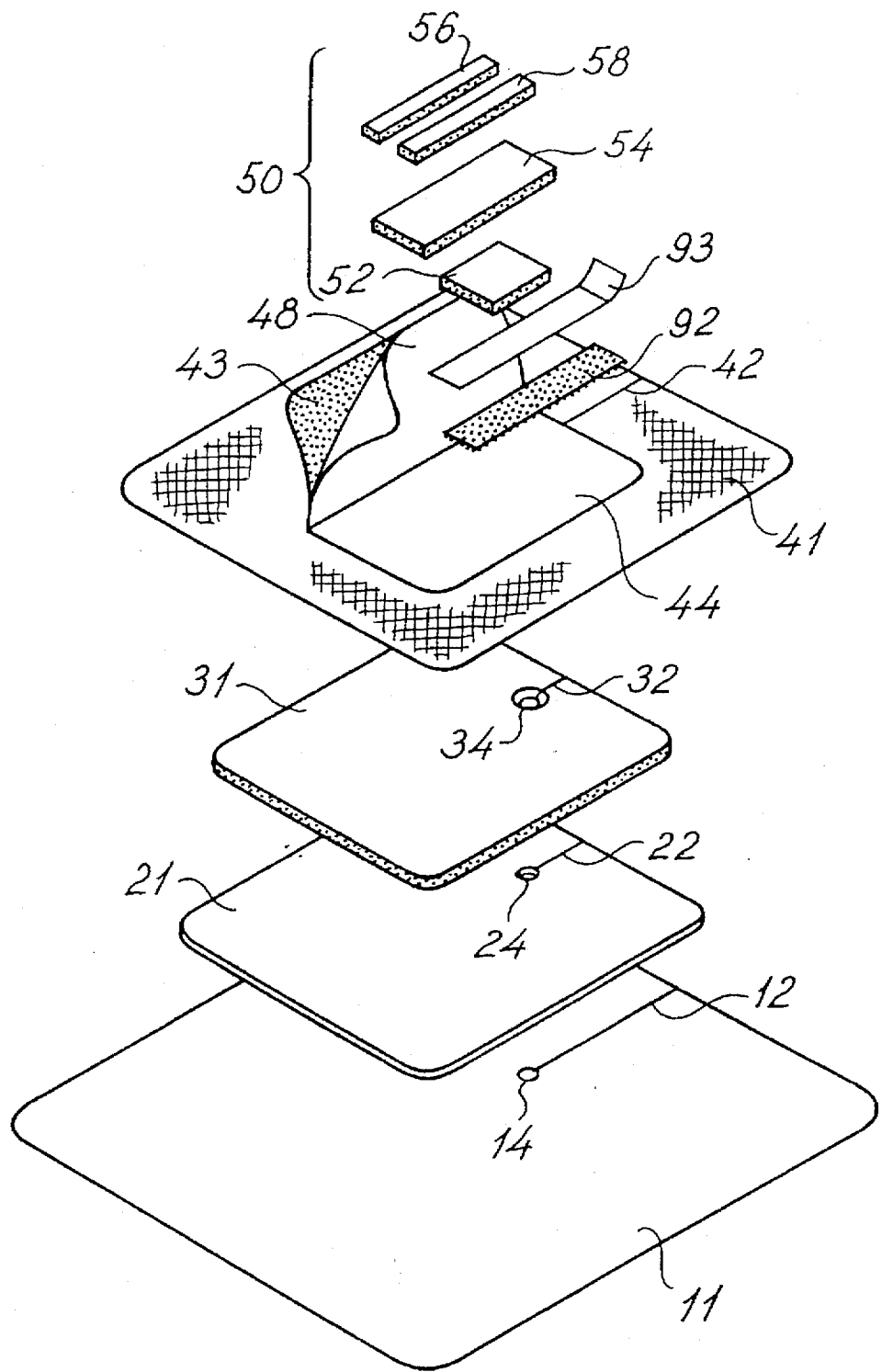
Figure 5:
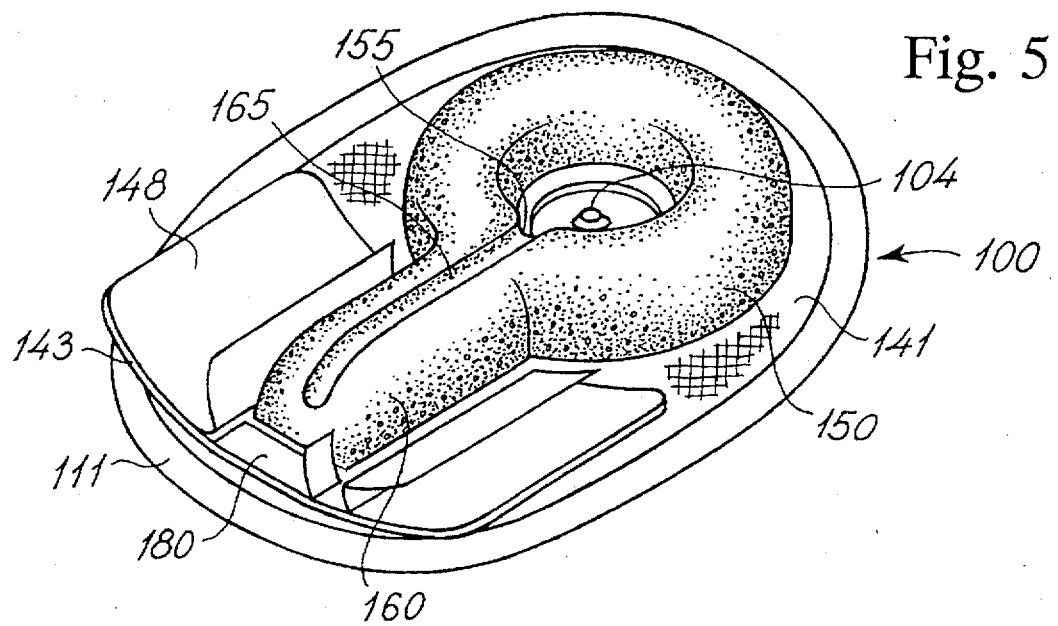
Figure 6:
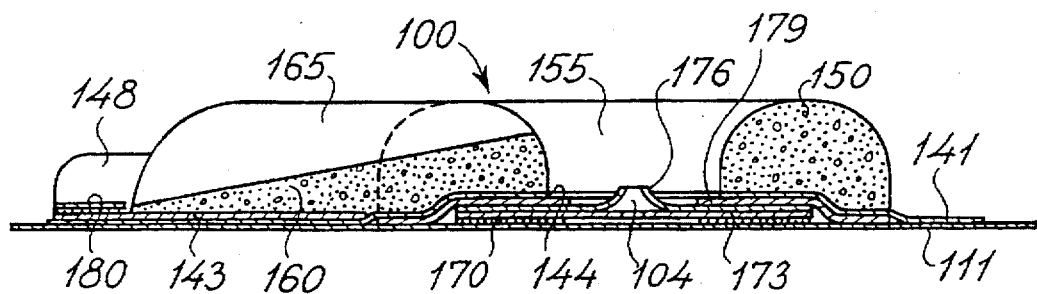
Figure 7:
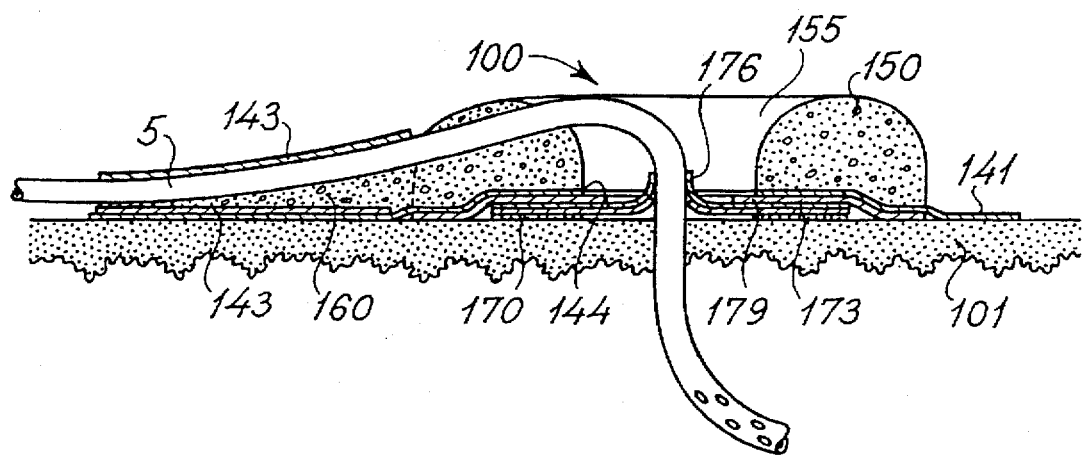

The present invention will now be further described with reference to the drawings, in which FIG. 1 is a schematical view of a first embodiment of a drainage tube fixating device according to the present invention, FIGS. 2 and 3 are schematical views illustrating the technique of applying the first embodiment of the device shown in FIG. 1, FIG. 4 is an exploded view of the first embodiment of the drainage tube assembly comprising the device according to the present invention shown in FIGS. 1–3, FIG. 5 is an schematic view of a second embodiment of the device for fixating a drainage tube, and particularly adapted for fixating pleural drainage tubes, FIGS. 6 and 7 are cross-sectional views of the device of FIG. 5, illustrating the device prior to use and in use, respectively.

Figure 8:
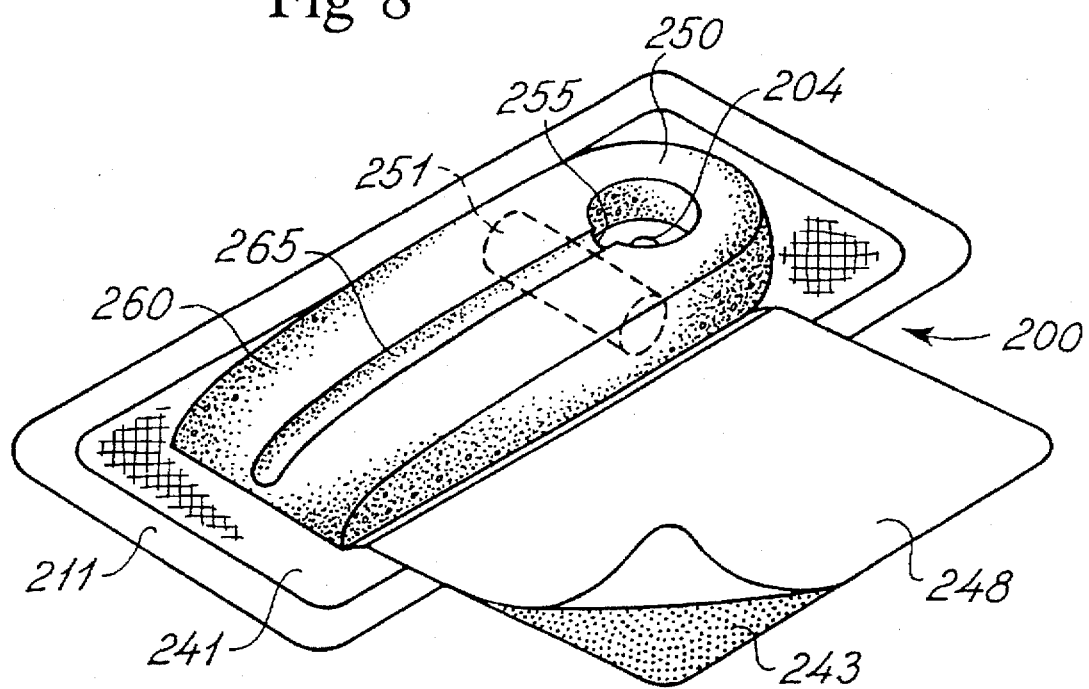
Figure 9:
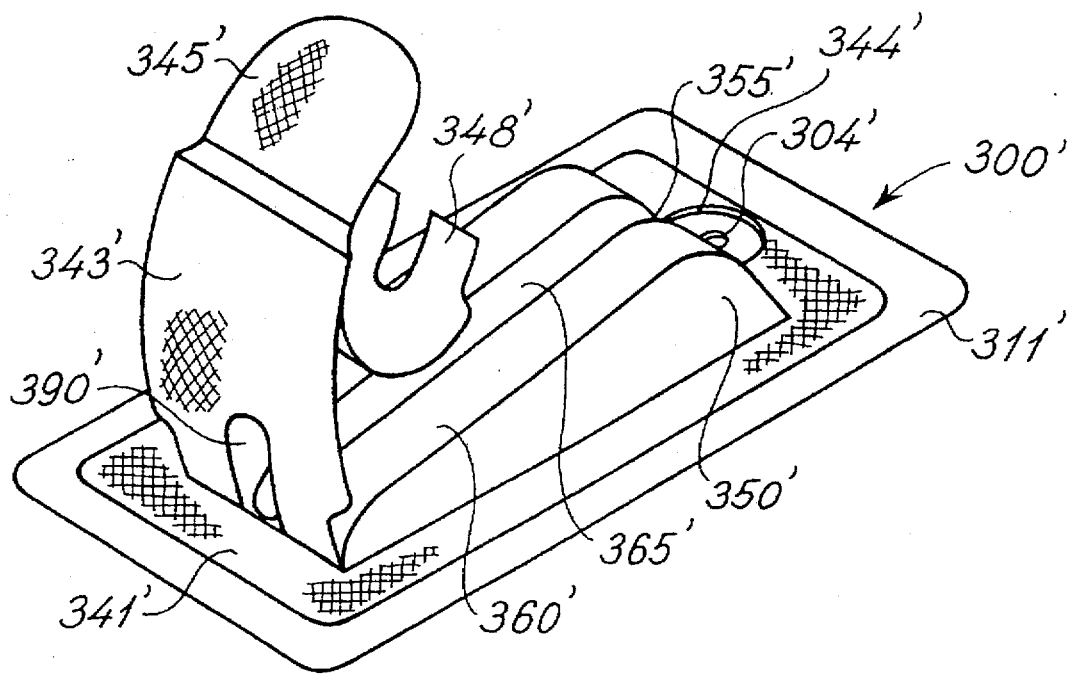
Figure 10:
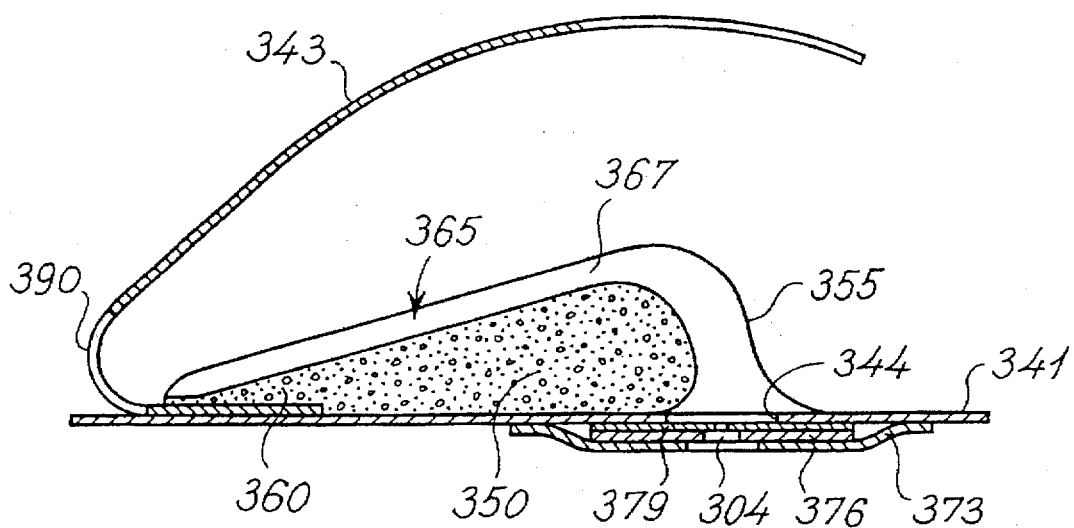
Figure 11:
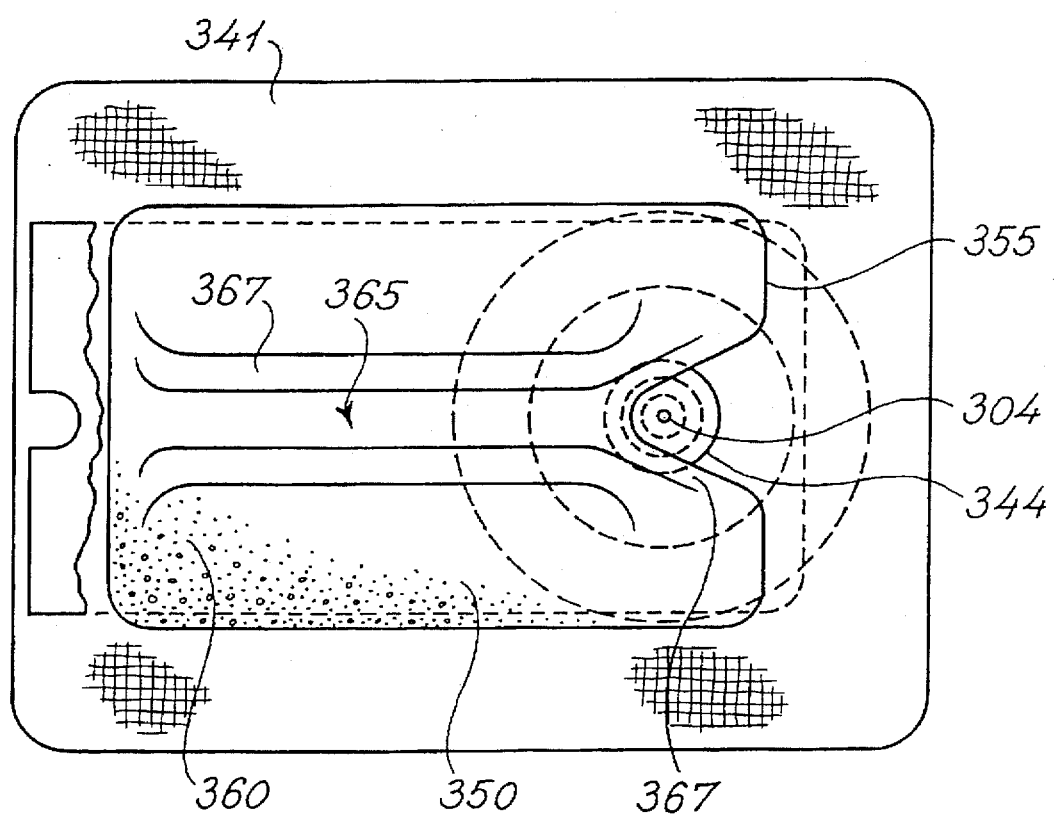
Figure 12:
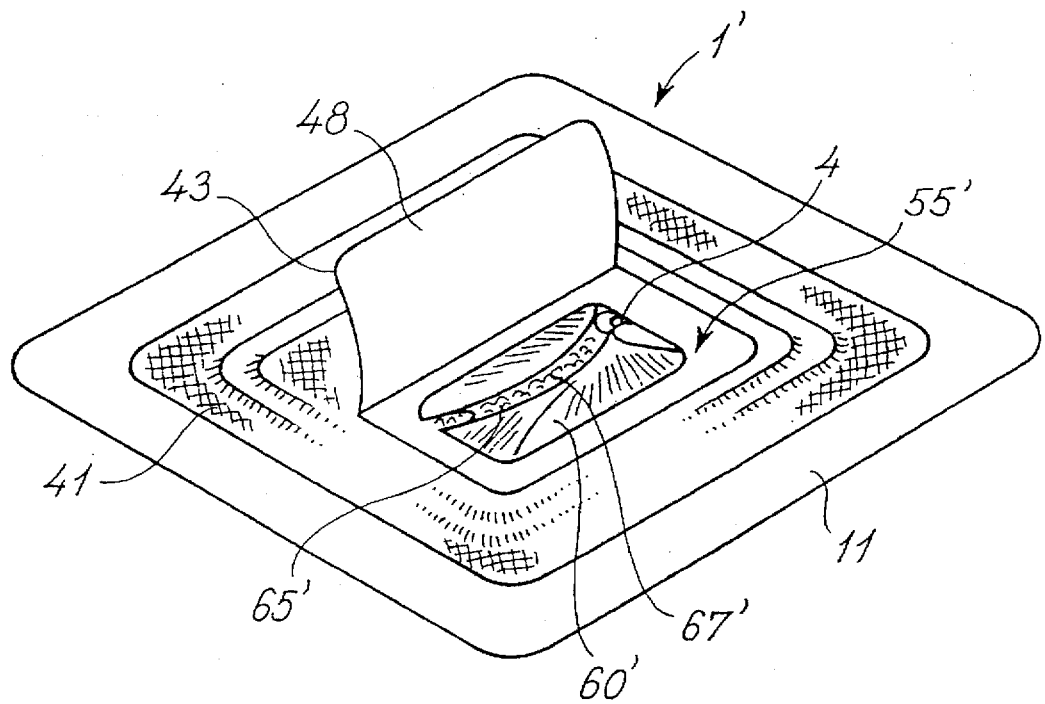

FIG. 8 is a view similar to the view of FIG. 5, illustrating a third embodiment of the device according to the present invention, FIG. 9 is a view similar to the view of FIG. 5, illustrating a fourth embodiment of the invention, FIG. 10 is a cross-sectional view of a fifth embodiment of the device for fixating a drainage tube according to the present invention, FIG. 11 is a top view of the device of FIG. 10, FIG. 12 is a schematical view of a sixth embodiment of a drainage tube fixating device according to the present invention.

Figure 16:
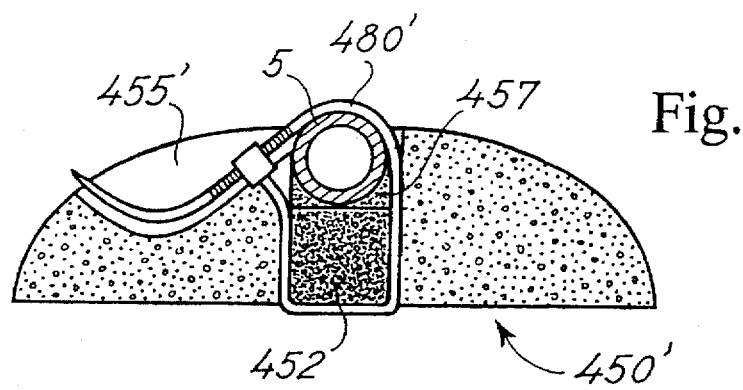
Figure 17:
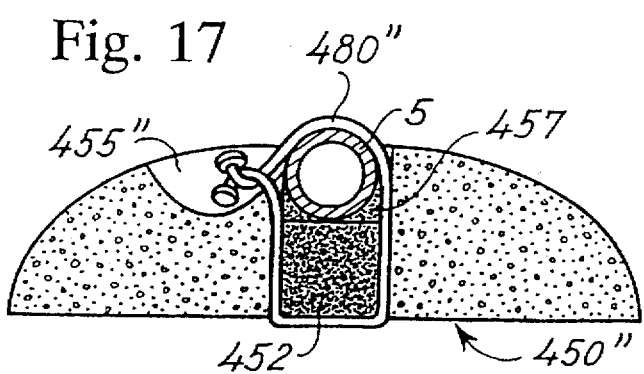
Figure 13:
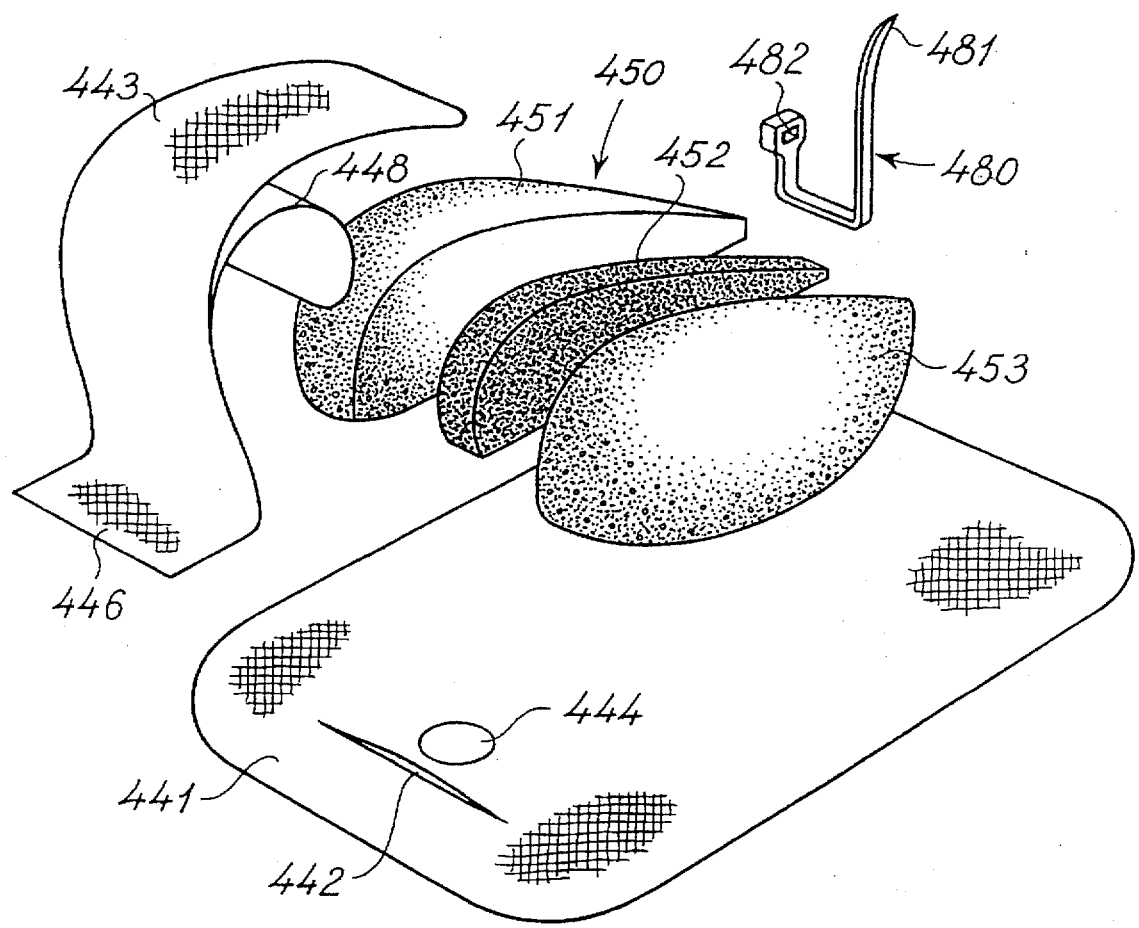
Figure 13:
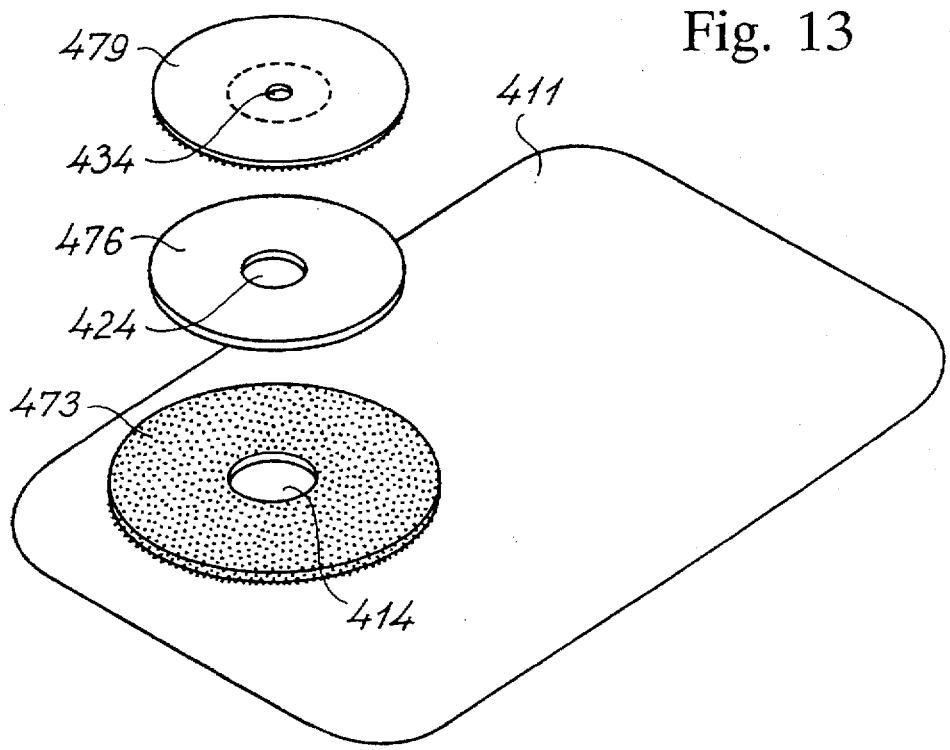
Figure 14:
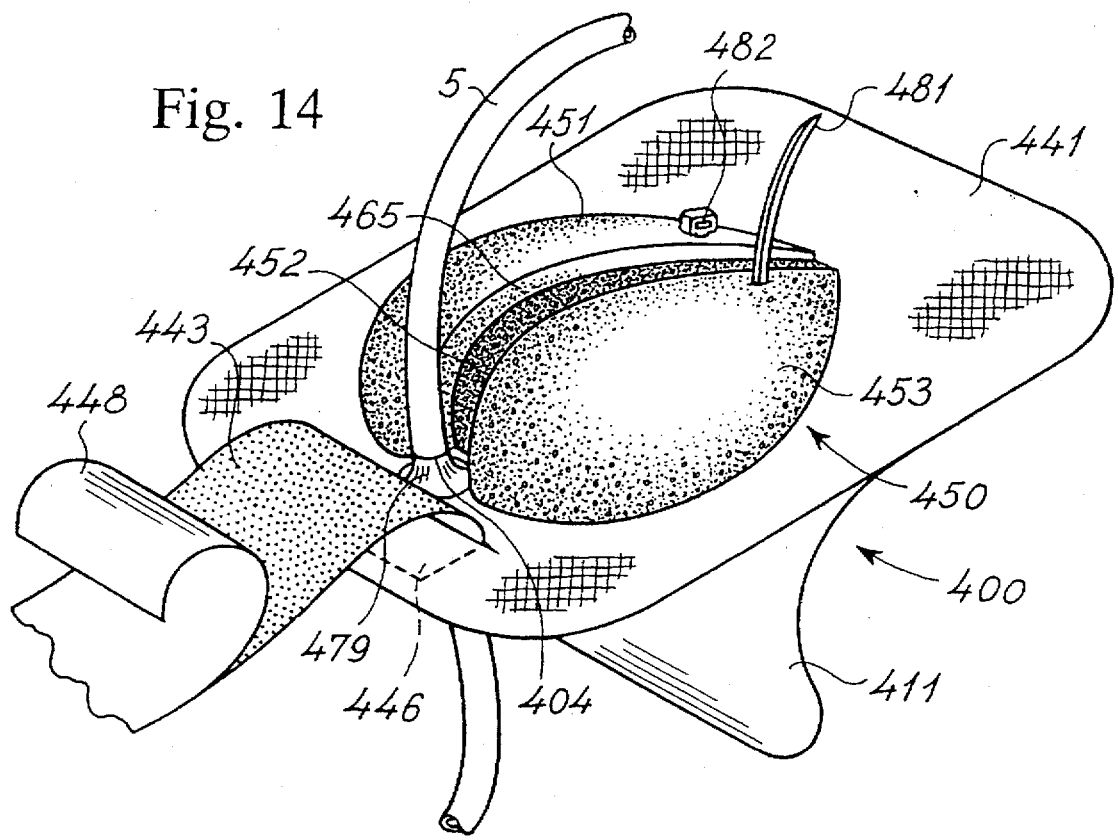
Figure 15:
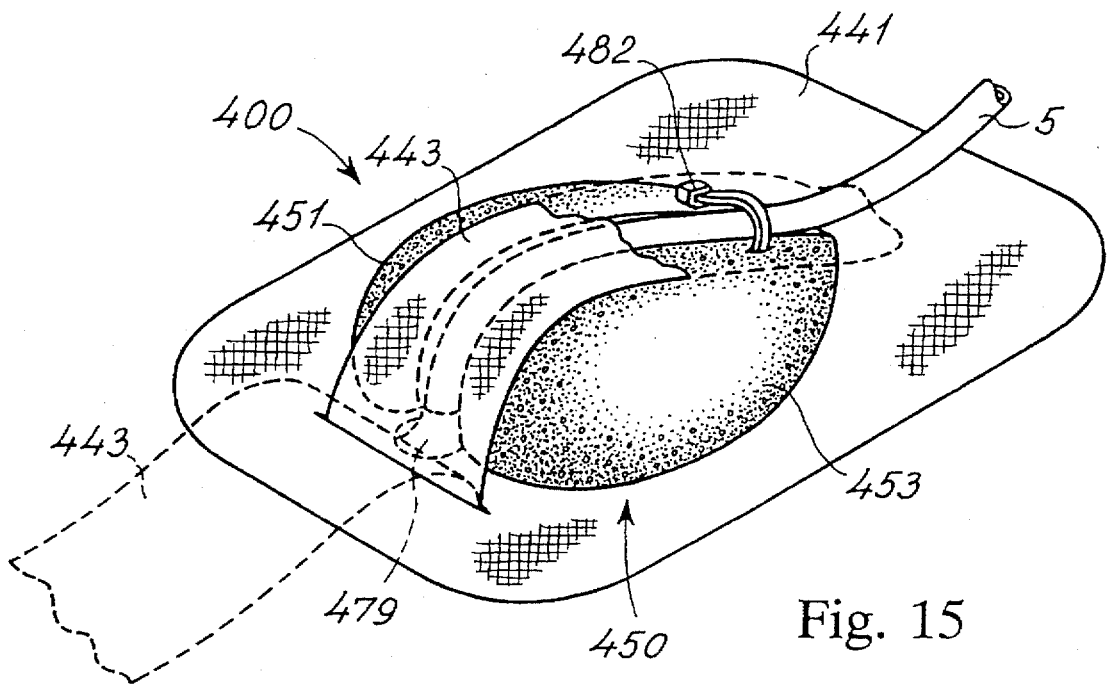

FIG. 13 is an exploded schematic view of a sixth embodiment of the device according to the present invention, FIGS. 14 and 15 are schematic views of the sixth embodiment of the device according to the present invention, prior to and after the fixation of a pleural drainage tube, and FIGS. 16 and 17 illustrate a cross-sectional view of alternative configurations of the support component of FIGS. 13–15.

In FIGS. 1–4, a first embodiment of a device for fixating a drainage tube is shown. The first embodiment shown in FIGS. 1–4, and to be described in greater details below, basically serves the purpose of fixating a joint-tube catheter relative to the skin of the patient without creating kinks or bends of the catheter.

The first embodiment of the device for fixating a drainage tube according to the present invention further serves the overall purpose of ensuring that the drainage tube does not become blocked due to the tube inadvertently being doubled or bent upon itself, thereby providing a drainage tube fixating device which render it extremely simple and far less complicated than hitherto to fixate drainage tube to a patient, further providing a reliable and lasting fixation.

As shown in FIG. 1 and as will be described in further details below, the device according to the first embodiment of the invention designated in its entirety the reference numeral 1 generally comprises a plaster component 41 having a central aperture and carrying an adhesive layer on the lower side thereof by means of which the plaster component 41 adheres to the skin surface of the patient to whom the device 1 is applied, a cover sheet 11 for covering said adhesive layer, a connecting component 31 having an aperture 4, a strip 43 carrying an adhesive layer and being provided with a cover sheet 48, and a support component generally indicated by the numeral 50 arranged adjacent said aperture 4 of the connecting component 31 and having a groove 65 for receiving a drainage tube in supporting relationship relative to the plaster component 41. The support component 50 is fixed to the upper surface of the connecting component 31 and protrudes from the upper surface of the plaster component through its central aperture. As shown, the support component 50 is formed with a slightly rounded or curved upper surface 60 providing a uniform support for a drainage tube being turned from an orientation substantially perpendicular to the skin surface of the patient to an orientation substantially parallel with the skin surface. The structure of the support component 50 will be explained in further details with reference to FIG. 4.

As shown in FIG. 2, illustrating the fixation of the device 1 according to the present invention to the body of the patient, the outer end of the drainage tube 5 which is a so-called pig-tail type drainage tube is inserted through the aperture 4 of the connecting component 31, i.e. a drainage tube which is provided with a distal end which is formed into the configuration of a pig-tail and which to a high degree resists the autonomous expelling of foreign bodies from the human body as compared to a straight line drainage tube.

Alternatively, as shown, the two areas of the device 1 delimited by a slit 2, may be forced apart, thus allowing the tube to be entered into the aperture 4. The cover sheet 11 is subsequently removed, exposing the adhesive layer of the plaster component 41. The device 1 is as a unitary structure shifted along the drainage tube 5 and is brought into facial contact with the outer skin surface of the patient.

FIG. 3 shows the device according to the invention, the plaster component having been fixated to the body of the patient. In this next step, the drainage tube 5 is bent to a position in which it extend substantially parallel to the skin surface of the patient. In this position, the drainage tube is being supported by the support component 50 located adjacent the aperture 4 through which the tube extends. The tube 5 is taken up by the groove 65 and the cover sheet 48 of a strip 43 is removed. By moving the securing strip 43 to the position shown on FIG. 3 in which the lower side of the securing strip 43, which may be provided with an adhesive layer, is in contact with the upper surface of the support component 50 and the drainage tube 5, the drainage tube 5 is secured and maintained in place in a position wherein the tube is turned to a position substantially parallel with the skin surface of the patient.

In FIG. 4, the various components of the first embodiment of the device according to the present invention is shown. The plaster component 41 as shown has an essentially rectangular outline but may take any convenient form according to the intended use. The plaster component 41 is provided with a central aperture 44 delimited along one side by an edge of a securing strip 43 formed as an integral part of the plaster component 41. At the lower side surface, the securing strip 43 is provided with an adhesive layer which is covered by the protective sheet 48. The plaster component 41 is furthermore provided with an elongated slit 42.

As illustrated, the device further comprises a connecting component 31 provided with a slit 32 and an aperture 34. The connecting component 31 is joined to the lower side surface of said plaster component 41, covering the central aperture 44, and extending beyond its limits. A further layer 21 arranged below the connecting component 31 provides a biologically acceptable contact between the device and the tissue at the entrance of the drainage tube. Layer 21 may carry a hydro-colloid component (not shown) on its lower surface, or may in fact itself constitute a hydro-colloid material. Connecting component 31 and layer 21 respectively may comprise an adhesive layer, or may be formed from an adhesive material, whereby the two layers may be joined.

The cover sheet 11 covers the exposed adhesive layer of the plaster component 41 and the exposed lower side surface of layer 21, possibly carrying a hydro-colloid component. Alternatively (not shown), two cover sheets of substantially identical configuration may be provided, the cover sheets adjoining one another along a line of separation extending substantially diametrically across the plaster component 41. The cover sheet may be provided with a slit 12 and an aperture 14.

The support component, generally indicated by the reference numeral 50 is formed from a pad 52, a supporting element 54 and elongated strips 56 and 58. The supporting element 54 may advantageously be provided with an adhesive layer, preferably a resin-based adhesive, which may be exposed to the ambience without loosing its adhesive property, on the upper side thereof. Thus, when the drainage tube 5 is taken up by the groove 65 as described above with reference to FIG. 3, which groove is formed by the two elongated strips 56, 58, the tube is fixated by means of the adhesive layer. The resinous adhesive may alternatively be provided on the top side of a separate strip which is provided with an ordinary adhesive on the lower side thereof, by means of which the separate strip is secured to the upper side of the supporting element 54 in the area forming the groove 65 between the elongated strips 56, 58. By virtue of the support component 50 being arranged on the top or upper surface of the connecting component 31, the support component 31 extends through the central aperture 44 of the plaster component 41. This structure allows the strip 43 to be formed as an integral part of the plaster component 41, the aperture 44 created during the formation of strip 43 at the same time serving as a through-going passage or aperture for the drainage tube 5. A strip of adhesive material 92 covered by cover strip 93 may be arranged alongside the support component on connecting component 31 with the purpose of providing an even more reliable securing of the securing strip 43 in the tube-retaining position shown on FIG. 3.

FIG. 12 shows an alternative embodiment 1' of the device according to the present invention. The device 1' of FIG. 12 resembles the device 1 of FIGS. 1–4, the support component 50 and the connecting component 31, however, having been replaced by a single and unitary bearing element 55', which may advantageously be formed by moulding. Thus, the bearing element 55' comprises a substantially flat or planar part and a supporting part 60' protruding therefrom. The supporting part 60' basically serves the same purpose as the support component 50 of FIGS. 1–4 and is provided with a groove 65', which is recessed in the surface of the supporting part 60' and extends from an area adjacent to the aperture 4 formed in the planar part and through which the drainage tube extends. The groove 65' forms one or several loops along its length for providing a firm hold on the drainage tube, and the groove may additionally be provided with an adhesive material 67', such as a resin-based adhesive which is applied to the basis of the groove. The walls of the groove 65' partly encompass the aperture 4, providing a lateral support of the entire drainage tube and providing a protective shielding of the drainage tube. The basis provides a supporting surface for a tube which is turned from an orientation substantially perpendicular to the skin-surface part of the patient and to an orientation substantially parallel with the skin-surface part of the patient.

Reference is now made to FIGS. 5–7 showing a second embodiment of the device 100 according to the invention and particularly adapted to be arranged at the thorax of a patient while at the same time creating a sealing of the entrance of a pleural drainage tube into the thorax of the patient in order to render it possible to create a vacuum within the cavity of the thorax of the patient so as to cause an adhesion of the pulmonary pleura of the patient to the costal pleura of the patient, and serving the purpose of correctly entering and positioning the drainage tube relative to the thorax of the patient. The device 100 shown in FIG. 5 generally comprises a plaster component 141 having an oval shape, and a support component 150 attached directly to the upper surface of the plaster component and protruding therefrom. The plaster component is provided with an adhesive on the lower side for fixating the plaster component 141 relative to a skin surface part of a patient or person. A cover sheet 111 covers the adhesive and is to be removed prior to the use of the device 100. The plaster component 141 is provided with a circular aperture delimited by a perimeter 144. The support component 150 is preferably made from a sponge-like material and is formed with a central aperture 155 arranged in registration with the aperture in the plaster component 141. The support component 150 is furthermore provided with an elongated section 160 having a groove 165 extending from the central aperture 155 and providing a lateral support for the drainage tube 5. The device is furthermore provided with securing strips 143 extending alongside the groove 165 and provided with an adhesive covered by cover sheet 148. The bottom surface of the groove 165, which may be provided with any suitable adhesive layer, is inclined and extends from an elevated point at the aperture 155 to a point at the other end of the elongated section 160 substantially at the level of the skin surface of the patient. Securing strips 143 may be folded to a position substantially covering the elongated section 160 and drainage tube 5, as shown on FIG. 7, whereby the pleural drainage tube 5 is fixated in an orientation substantially parallel with the skin surface of patient 101.

Referring now to FIGS. 6 and 7 in particular, the device 100 further comprises a composite structure including a plurality of annular components designated the reference numerals 170–179 fixed to the lower side of the support component 150 at the aperture 155, which components are provided with through-going apertures which are positioned in registration together defining an aperture 104 through which the drainage tube 5 is passed. The composite structure including the annular components 170–179, firstly comprises a glue layer 170 which is a hydro-colloid glue carried by an annular element 173. On top of the annular element 173, an annular membrane 176 is positioned which annular membrane is formed with a central aperture of a diameter adapted to the diameter of the drainage tube, thus sealing the aperture 104 of the device relative to the drainage tube 5. Between the membrane 176 and the plaster component 141 an annular plate member 179 is arranged.

The elongated strip 143 extends beyond the sides of an elongated section 160 and is sandwiched between the elongated section 160 and the plaster component 141. As shown, a drainage tube which is a pleural drainage tube extends from the body 101 of the person or patient substantially perpendicularly. The pleural drainage tube 5 is fixated and sealed relative to the patient 101 by means of the device 100.

In use, the cover sheet 111 is initially removed. The adhesive layer at the lower side surface of the plaster component 141 together with the annular hydro-colloid component 170 is caused to adhere to the skin surface part of the patient. The annular hydro-colloid component 170 additionally serves the purpose of providing a seal between the plaster component 141 and an annular skin surface part of the patient, which skin surface part encircles the pleural drainage tube 5 and further the aperture of the skin through which the pleural drainage tube 5 is entered into the cavity of the thorax. The sealing membrane 176 provides a hermetical seal between the aperture of the skin surface part through which the pleural drainage tube 5 is entered into the cavity of the thorax and the environment. In FIG. 7 the device 100 is shown after the device has been applied to the patient, and clearly illustrates the facial adhesive contact between the device 100 and the outer skin surface part of the patient 101 established by means of the plaster component 141 and further by means of the annular hydro-colloid component 170 which is glued or adhered to the lower side surface of the annular carrier element 173 by means of an annular adhesive tape (not shown). From FIG. 7, it is also evident that the support component 150 supports the pleural drainage tube 5 at the entrance through the skin surface part of the patient and prevents the pleural drainage tube 5 from forming kinks or being bent upon itself.

FIGS. 8 and 9 are views similar to the view of FIG. 5, illustrating a third and fourth alternative embodiment according to the present invention, which embodiments are designated the reference numerals 200 and 300', respectively, and basically serve the purpose of supporting a pleural drainage tube as described with reference to FIGS. 5–7. The device 200 of FIG. 8 comprises a support component 250 similar to the component 150 of the device 100 described above with reference to FIGS. 5–7, which component 250 comprises an elongated section 260 having a groove 265 formed therein. The support component is made from a soft, sponge-like material and is provided with a circular aperture 255 which encompasses an aperture 204 of a plaster component 241. A rigid, tubular element 251 provides additional support of a part of a drainage tube which passes through the aperture 204 and is received by the groove 265.

The drainage tube, e.g. the drainage tube 5 shown in FIGS. 2 and 7, is fixated relative to the plaster component 241 of the device 200 using a strip 243 similar to the above described strips 43 and 143 which is arranged on the plaster component and provided with an adhesive layer. The strip 243 may extend along the entire length of the support component and may be transparent in the region of the aperture 255 whereby the proper positioning of the drainage tube may be checked.

In FIG. 9, the device 300' is shown comprising a plaster component 341' and having an aperture 304' for a pleural drainage tube (not shown). An adhesive has been applied to the lower side of the plaster component which is covered by a cover sheet 311'. A support component 350' comprises an inclined, leading edge 355' arranged adjacent to the aperture 344' and is provided with a groove 365' formed in the leading edge 355' and in the top surface of the support component 350' and extending to a distal portion 360' thereof, for receiving and providing lateral support for the drainage tube. As shown in FIG. 9, the groove 365' is provided with a rounded bottom surface leading the drainage tube in a soft curve to a position substantially parallel to the body of the patient at the distal portion 360'.

FIG. 10 and FIG. 11 show a device according to a fifth embodiment of the invention similar to the device described with reference to FIG. 9, the reference numerals indicating the same elements as in FIG. 9, however, with the omission of the '. The embodiment of FIG. 10 and FIG. 11 differs from the device of FIG. 9 in that the walls 367 of the groove 365 partly encompass the aperture 304, whereby a drainage tube (not shown) extending from the aperture 304 is supported laterally from that point by the walls 367. Thus, the support component 350 provides a support for a length of the drainage tube extending from the aperture 304 to the distal portion 360 of the support component 350, thus ensuring that the tube is at no position bent upon itself. An elongated strip 343 is preferably joined to the plaster component 341 at the distal portion 360 of the support component, a distal part of the strip 343 being sandwiched between the support component and the plaster component. As shown, the elongated strip 343 is formed with a passage 390 for the drainage tube and is on one surface provided with an adhesive covered by a cover sheet 348. When the cover sheet 348 is peeled off and the strip 343 is bent downwards for adhering against the upper surface of the support component, the drainage tube is effectively joined or locked within the groove 365, and any upwardly directed force on the part of the tube which extends parallel to the skin surface of the patient in the area of the passage 390 is transmitted directly to the root of the elongated strip 343.

FIG. 10 furthermore shows a composite structure 373–379, primarily serving the purpose of sealing the aperture 304 in relation to a drainage tube. The composite structure basically comprises the same components as the composite structure illustrated in FIG. 6 and FIG. 7, i.e. a carrier element 373, an annular membrane 376 and an annular plate member 379, defining the aperture 304 together with an aperture 344 formed in the plaster component 341.

Reference is now made to FIGS. 13–17 which show a sixth embodiment 400 of the device according to the present invention. As best seen in FIG. 14, the device 400 basically resembles the device shown in FIGS. 10 and 11. Thus, the device 400 generally comprises a support component 450 which is attached directly to the upper surface of a plaster component 441, the device 400 being provided with a through-going aperture 404 for a pleural drainage tube. The support component is provided with an elongated, groove-like recess 465 arranged in a surface part thereof. As shown in FIG. 13, the plaster component 441 is provided with an aperture 444 and the support component 450 is attached to the plaster component 441 such that the walls of the groove 465 partly encompass the aperture 444 in basically the same manner as described with reference to FIGS. 10 and 11. Similarly, the device 400 comprises a composite struture 473–479 which is adhesively secured to the lower side of the plaster component 441.

The composite structure 473–479 basically comprises three superimposed and disc-like elements 473, 476, 479, each being formed with a central, circular aperture 414, 424, 434, respectively. The composite structure 473–479 is adhesively secured to the plaster component 441 such that the apertures 414, 424, 434 are in registration with the aperture 444 formed in the plaster component 441, thus providing the central through-going aperture 404 of the device 400. The disc-like element 473 is basically a layer of a hydro-colloid substance while the element 476 is formed from silicone. The element 479 serves as a membrane and provides a seal between the through-going aperture 404 of the device 400 and a pleural drainage tube 5, as shown in FIG. 14. The aperture 414 formed in the hydro-colloid layer 473 corresponds in size to the aperture 444 formed in the plaster component 441 and the diameter thereof is somewhat larger than the diameter of the drainage tube 5, to allow the drainage tube 5 to extend through the aperture 404 of the device without causing damage to the hydro-colloid layer 473. The aperture 424 formed in the element 476 has a diameter which substantially corresponds to the diameter of the drainage tube while the aperture 434 in the membrane 479 is somewhat smaller than the diameter of the drainage tube for providing a sealing effect. A further rigid and annular element (non shown) may be arranged between the membrane 479 and the lower side of the plaster component 441 for providing a rigid holding means which may be grasped by the user during the application of the device i.e. as the drainage tube is drawn or otherwise passed through the aperture 404 of the device 400.

The device 400 also differs from the embodiment of the invention illustrated in FIGS. 10 and 11 in that the support component 450 is formed from three individual elements 451, 452, 453. The elements 451 and 453, which are formed from a relatively soft foamed material, are adhesively joined to a respective vertical side of the central element 452, which is formed from a relatively hard or rigid foamed material. The element 452 is provided with an upper, rounded surface which serves to support the drainage tube 5, as indicated in FIG. 15. The dimensions and configuration of the element 452 relative to the elements 451 and 453 is such that the element 452 forms the recessed or groove-like part 465 of the support component 450 whereby the elements 451, 453 provide a lateral support for the drainage tube 5 when the drainage tube 5 is in the in use-position as shown in FIG. 15 and as it will be described in further details below.

The support component 450 is furthermore provided with a tie 480 formed as a flexible band which is arranged so as to partly encompass the element 452 at the end thereof most distant from the aperture 404. The tie 480 is secured in a position surrounding the element 452 either by being threaded through the elements 451 and 453 as illustrated in FIGS. 14 and 15, or by being arranged surrounding the central element 452 prior to the forming of the support component 450, as illustrated in FIGS. 16 and 17, and being secured in said position by means of an adhesive. One end 481 of the tie 480 may be provided with barbs while the other end 482 may be provided with an opening through which the free end 481 is drawn in a non-releasable manner by means of the barbs.

The device 400 is furthermore provided with an elongated securing strip 443 carrying an adhesive on one side together with a cover sheet which may be removed for exposing the adhesive. One end 446 of the securing strip 443 extends through a slit-like opening 442 arranged in the plaster component 441 adjacent to the aperture 444. The upper surface of the end 446 of the securing strip 443 is in contact with adhesive material on the lower side of the plaster component 441 whereby the securing strip 443 is fixed relative to the plaster component 441.

In use, the drainage tube 5 is pulled through the aperture 404 formed in the device 400 as shown in FIG. 14. The membrane 479 fits tightly around the tube 5, thus sealing the point of entrance of the plural drainage tube into the body of the patient. Following this step, the drainage tube 5 is manually bent downwards to assume the position shown in FIG. 15, wherein the tube 5 is continuously supported by the rounded bottom surface of the groove 465 formed by the rounded upper surface part of the element 452 which forms the central part of the support component 450. The walls of the groove prevents the drainage tube 5 from shifting in a lateral direction. In this position, the drainage tube 5 is secured to the support component by means of the tie 480 and the securing strip 443, which is bent downwards to adhere against the upper surfaces of the support component and the drainage tube 5, respectively.

FIGS. 16 and 17 illustrate cross-sectional views of alternative configurations of the support component 450. The support component 450' of FIG. 16 is provided with a recess 455' for taking up a free end of the tie 480'. The support component 450" of FIG. 17 is provided with a similar recess 455" for taking up the free ends of a tie 480" which is operative to secure the drainage tube 5 in position by simply twisting its ends as illustrated schematically. As shown in FIGS. 16 and 17, a adhesive material 457, such as a resin based adhesive, may be applied to the basis of the groove.

It is to be realized that the embodiments described above with reference to FIGS. 1–17 may be modified in numerous ways and further combined so as to provide a device for fixating a drainage tube and optionally for sealing the drainage tube or the aperture of the skin surface part through which the drainage tube extends. Likewise, it is to be understood that the drainage tube may be replaced by any other tube suitable for introducing a medium into the body of the patient.

EXAMPLE

A prototype implementation of the presently preferred embodiment of the device according to the present invention shown in FIGS. 1–4 and designated the reference numeral 1, was made from the following components.

The connecting component 31 was made of a PE foam. Its dimensions were 60×50×1.5 mm, the slit 32 having a length of 5 mm. The layer 21 of a hydro-colloidal material, having a thickness of 1 mm, was applied to the lower surface of the component 31. The inner diameter of the aperture 34 was 4 mm. The connecting component 31 was joined to the lower or first side surface of plaster component 41 by means of the acrylic adhesive on the lower side surface of the plaster component 41. The plaster component 41 was formed from non-woven polyamide, and the central opening or aperture 44, having dimensions of 30×50 mm, was formed by cutting-out the segment 43 forming the securing strip 43 and integrally connected to the plaster component 41 along one edge. The connecting component 31 when joined to the plaster component 41 covered the entire aperture 41 formed therein. Support component 50 was joined to the upper surface of the connecting component 31 so as to protrude through the aperture 44 formed in plaster component 41. The support component 50 was formed from four separate elements: the elongated strips 56, 58 made from a PE foam and having dimensions of 4×30×5 mm and superposed on the supporting element 54 made from PE foam, and having dimensions of 30×10×1.5 mm, and the underlying pad 52 made from PE foam and having dimensions of 15×10×1.5 mm. The elongated strips 56, 58 were placed parallel to one another with a spacing of 2 mm, forming the tube-receiving groove 65, and the pad 52 was arranged underlying one end of the supporting element 54, thus raising part of the elongated strips corresponding to the thickness of the pad.

I claim:

1. A catheter or tube assembly for fixing a tube, such as a drainage tube inserted through an opening in a patient's skin, relative to the patient's skin, comprising:

a catheter or tube forming a drainage tube;

a plaster component including a support foil having an aperture for receiving said drainage tube and having opposite first and second side surfaces, said first side surface being provided with an adhesive layer for fixing said plaster component relative to the patient's skin, an outer support component arranged above said plaster component and adjacent said aperture at said second side surface of said plaster component and protruding therefrom, said outer support component having an outer surface for supporting a length of said tube extending from said aperture at said second side surface of said plaster component for bending, without kinking, said length of said tube in supported relationship with said outer support component from an orientation substantially perpendicular to the patient's skin to an orientation substantially parallel with the patient's skin, and said outer support component and said plaster component being joined together said assembly further including a cover for covering the outer support component and tube assembly.

2. The catheter or tube assembly according to claim 1 wherein said outer surface of said support component is rounded for supporting said length of said tube in a curved configuration.

3. The catheter or tube assembly according to claim 1 wherein said plaster component and said support component are joined together by means of a connecting component.

4. The catheter or tube assembly according to claim 3 wherein said connecting component is provided with an aperture, said connecting component being attached to said first side surface of said plaster component, and said aperture of said connecting component being in registration with said aperture of said plaster component.

5. A catheter or tube assembly for fixing a tube, such as a drainage tube, inserted through an opening in a patient's skin, relative to the patient's skin, comprising:

a catheter or tube forming a drainage tube;

a plaster component including a support foil having an aperture for receiving said drainage tube and having opposite first and second side surfaces, said first side surface being provided with an adhesive layer for fixing said plaster component relative to the patient's skin, an outer support component arranged above said plaster component and adjacent said aperture and said second side surface of said plaster component and protruding therefrom, said outer support component having an outer surface for supporting a length of said tube extending from said aperture at said second side surface of said plaster component for bending, without kinking, said length of said tube in supported relationship with said outer support component from an orientation substantially perpendicular to the patient's skin to an orientation substantially parallel with the patient's skin, and said outer support component and said plaster component being joined together and said outer support component providing lateral support of said length of the drainage tube said assembly further including a cover for covering the outer support component and tube assembly.

6. A catheter or tube assembly for fixing a tube, such as a drainage tube, inserted through an opening in a patient's skin, relative to the patient's skin, comprising:

a catheter or tube forming a drainage tube;

a plaster component including a support foil having an aperture for receiving said drainage tube and having opposite first and second side surfaces, said first side surface being provided with an adhesive layer for fixing said plaster component relative to the patient's skin, an outer support component arranged above said plaster component and adjacent said aperture and said second side surface of said plaster component and protruding therefrom, said outer support component having an outer surface for supporting a length of said tube extending from said aperture at said second side surface of said plaster component for bending, without kinking, said length of said tube in supported relationship with said outer support component from an orientation substantially perpendicular to the patient's skin to an orientation substantially parallel with the patient's skin, and said outer support component and said plaster component being joined together, and securing means for securing said length of said tube relative to said plaster component said assembly further including a cover for covering the outer support component and tube assembly.

7. The catheter or tube assembly according to claim 6 wherein said securing means forms an integral part of said support component.

8. A catheter or tube assembly according to claim 6 wherein said securing means is integrally connected to the plaster component.

9. The catheter or tube assembly according to claim 6 wherein said securing means comprises an adhesive strip for fixing said tube.

10. A catheter or tube assembly according to claim 9 wherein said adhesive strip is provided with a transparent area in the area of the aperture in said plaster component.

11. The catheter or tube assembly according to claim 1 wherein said support component has an aperture and is made from a sponge-like material, said aperture being in registration with said aperture in said plaster component.

12. A catheter or tube assembly according to claim 1 further comprising sealing means between said plaster component and the patient's skin for sealing around said aperture in said plaster component relative to the outer periphery of the drainage tube.

* * * * *